United States Patent [19]

Shaw

[11] Patent Number: 5,254,122
[45] Date of Patent: Oct. 19, 1993

[54] LONGITUDINALLY EXTENDING SPLICING BAND FOR BODY OR LIMB ENCIRCLING THERAPEUTIC DEVICE

[76] Inventor: Frank D. Shaw, 18 Oakwood La., Rumson, N.J. 07760

[21] Appl. No.: 919,055

[22] Filed: Jul. 23, 1992

[51] Int. Cl.$^5$ .................................. A61B 17/00
[52] U.S. Cl. .................................. 606/201
[58] Field of Search .............. 128/869, 870, 876, 877, 128/878, 882; 606/201, 202, 203

[56] References Cited

U.S. PATENT DOCUMENTS 1,970,042  8/1934  Brathwaite .................... 606/202
4,215,687  8/1980  Shaw ........................ 128/DIG. 15

Primary Examiner—C. Fred Rosenbaum
Assistant Examiner—Noelle Kent Gring
Attorney, Agent, or Firm—Brumbaugh, Graves, Donohue & Raymond

[57] ABSTRACT

A slide fastener splicing band for use in splicing a therapeutic compression device embodying a plurality of parallel compression bands for applying compression to a body or a limb and from which intermediate portions of the compression bands are removed to shorten them to the desired lengths for encompassing the body or limb to which compression is to be applied. A therapeutic compression device embodying a slide fastener splicing tape to facilitate removal of the therapeutic compression device from the body or limb and reapplication of the device to the body or limb.

5 Claims, 2 Drawing Sheets

001
LONGITUDINALLY EXTENDING SPLICING BAND FOR BODY OR LIMB ENCIRCLING THERAPEUTIC DEVICE

BACKGROUND OF THE INVENTION

This invention relates to a body or limb encircling therapeutic device, and more particularly to a device of this type which includes a longitudinally extending splicing band which facilitates assembly of the device and, after being assembled, facilitates quick and easy removal of the device from the body or limb and reapplication to the body or limb.

Facilitating removal and reapplication of such therapeutic devices has always presented a problem, but now that these devices are being developed for NASA to reduce the effects of microgravity on astronauts, a solution to the problem of quick removal and reapplication has taken on increased importance.

Therapeutic compression devices of this general type are described in my U.S. Pat. No. 4,215,687 which description is incorporated herein. This device is made up of an assembly of compression bands which are available in different lengths, depending on the girth of the portion of the body or limb to be encompassed. Since the selected lengths of the compression bands are generally longer than necessary, in use, intermediate lengths of the band are usually removed and spliced to reduce the lengths of the bands to the desired lengths. When the bands have been properly spliced to the desired lengths, the bands are tightened and anchored around the body or limb.

In my U.S. Pat. No. 4,215,687, a plurality of parallel compression bands are spliced by interposing a perpendicular anchoring tape between the cut ends of the bands, the anchoring tape having the same outer interlocking fastening surface as the outer surfaces of the compression bands, and then placing a plurality of splicing elements across the anchoring tape and the cut ends, the inner fastening surface of the splicing element interlocking with the outer surface of the anchoring tape and the outer surfaces adjacent the cut ends of the compression bands. An assembled therapeutic device spliced in this manner is removed from the body or limb by unthreading all the compression bands.

My U.S. Pat. No. 5,120,300 relates to a compression band for quick and easy application one at a time to a body or limb in which, after a quick application, the compression band can be tightened to apply the desired compression. This compression band, however, does not facilitate the removal and reapplication of an assembly of therapeutic compression bands applied to the body or a limb.

SUMMARY OF THE INVENTION

The present invention relates to a body or limb encircling therapeutic device made up of a plurality of body or limb encircling compression bands arranged in edge-to-edge relationship and having intermediate cut ends spliced together by a longitudinally extending splicing band extending perpendicularly to the compression bands with the width spanning the cut ends, the longitudinally extending splicing band preferably embodying a slide fastener. The slide fastener splicing band is located opposite the overlapping ends of the compression bands which are used to tighten the bands. The assembly encompasses the girth of the body or limb, and the compression bands are individually tightened and held in the tightened condition to apply therapeutic compression to a portion of the body or limb. The therapeutic device can be easily and quickly removed by releasing the tension of each individual band and then opening the slide fastener to separate the longitudinal portions of the splicing band so that the therapeutic device can be removed. The therapeutic device can be quickly and easily reapplied to the body or limb by closing the slide fastener and then retightening the individual compression bands.

The present invention eliminates the perpendicular anchoring tape required in the therapeutic compression device of my U.S. Pat. No. 4,215,687 and replaces the plurality of splicing elements with a single slide fastener splicing band, thus significantly reducing complexity, number of components, bulk and cost. Custom fitting is also greatly simplified and expedited.

Also, when removing the device, it is no longer necessary to turn back the ends of every band and engage their hook tape ends with their own side surfaces in order to avoid their attachment to the surfaces of other bands. Such random attachments results in intolerable entanglement of bands.

With the present invention, many persons who are disabled to the extent that they are unable to thread, turn back and rethread the band ends of my earlier compression device, and are thus denied its therapy, can readily loosen the bands, tighten the bands and operate the slide fastener of the present invention.

DESCRIPTION OF THE DRAWINGS

For a complete understanding of the present invention, reference can be made to the detailed description which follows and to the accompanying drawings in which.

DETAILED DESCRIPTION OF PREFERRED EMBODIMENTS

Figure 2:
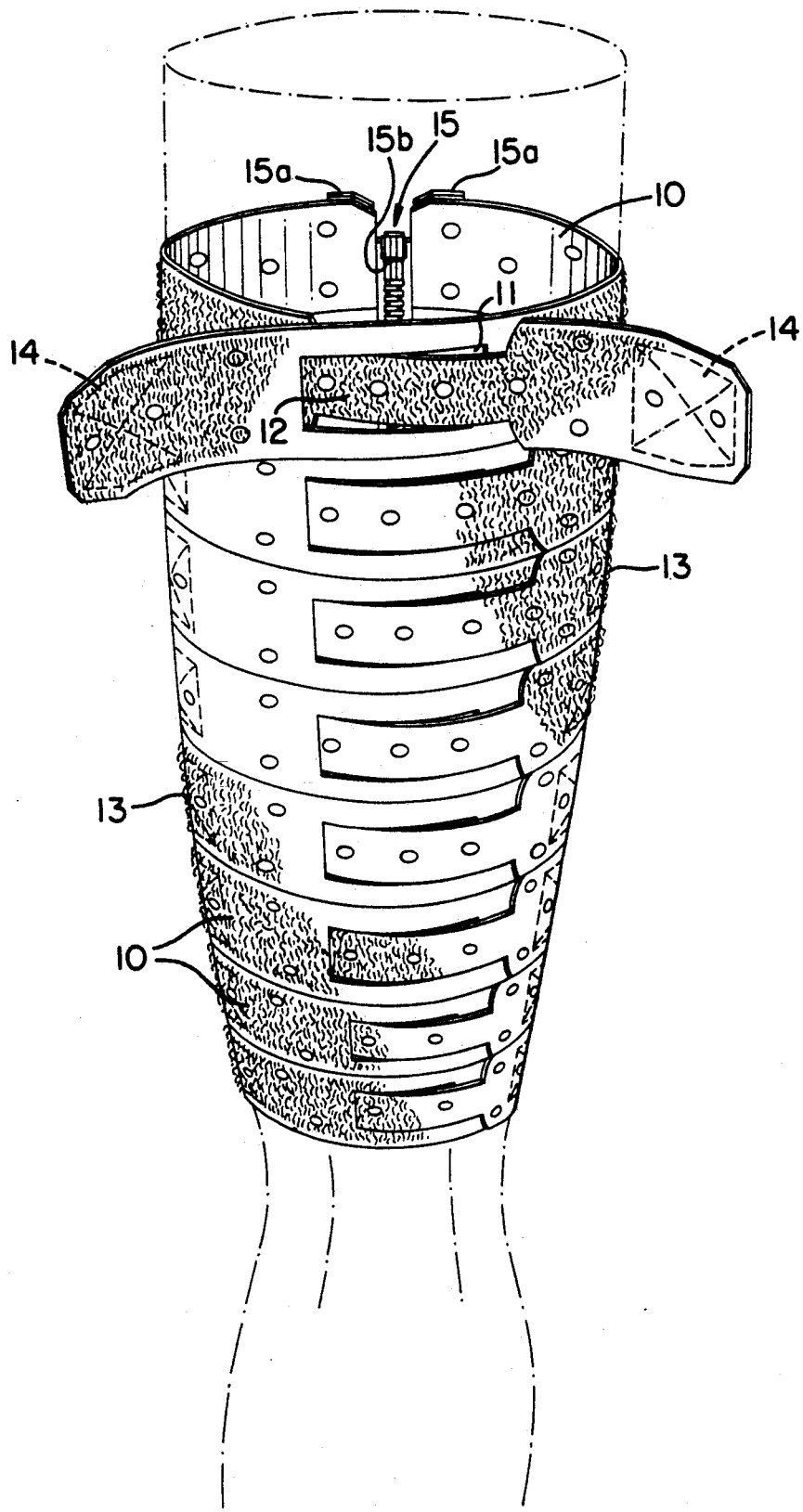
FIG. 2 is a perspective view showing the therapeutic compression device applied to a limb with the slide fastener closed.

A compression therapeutic device embodying the present invention, shown in the drawings as a legging, is an assembly made up of a plurality of compression bands 10 arranged in parallel, edge-to-edge relationship to encompass a part of a leg. Each compression band has a slot 11 at one end and a narrow portion 12 at the other end so that the band can be applied to the leg and tightened by inserting the narrow portion through the slot, as shown at the top of FIG. 2, and pulling the threaded ends in opposite directions. Each band is held in tightened condition by VELCRO or similar fastening surfaces on the inner surfaces of the ends of the band and on the outer surface of the band.

The bands are preferably made a strong flexible and non-stretchable material. The inner surface is preferably relatively smooth to engage the skin or a stocking. The outer surface of the band has a fastening surface thereon, preferably an interlocking VELCRO nap material 13 secured to the surface of the band. As shown, it is applied continuously along the outer surface, that is to say the surface opposite the surface which interfaces with the body. The extreme ends of the inner surface of the band have fastening pieces or patches 14, preferably VELCRO hook surfaces, which interlock with the fastening surface 13 on the outer surface of the band. Thus, when the bands are wrapped around the body or limb and the narrow portion 12 at one end is inserted through the slot 11 at the opposite end and the ends are drawn apart to tighten the band, as shown in FIG. 2, the band can be held in the tightened condition by pressing the interlocking surfaces 14 against the underlying interlocking surfaces 13. In the tightened condition the narrow portion of the band is accommodated within the slot 11.

The lengths of the bands supplied are ordinarily longer than the circumference or girth of the body or limb about which they are to be wrapped, and it is the usual practice to adjust the length of the band to the circumference or girth of the body or limb to be encompassed by removing an intermediate span. The cut ends are then spliced together.

The splicing is accomplished in the present invention by a slide fastener band 15 which extends perpendicularly to the compression bands with the width spanning the cut ends. The slide fastener splicing band 15 is made up of a pair of longitudinal portions 15a having inner fastening surfaces, preferably VELCRO mushroom hook surfaces, which interlock with the outer fastening surfaces of the compression band adjacent the cut ends thereof and a slide fastener 15b which joins and separates these longitudinal portions. The slide fastener splicing band 15 is placed in contact with the cut ends of the compression bands with the slide fastener closed so that the width of the slide fastener splicing band spans the cut ends of the compression bands, holding them in assembled condition. The assembled device with the slide fastener splicing band opened to separate the longitudinal portions 15a, as shown in FIG. 1, is wrapped around the leg, the slide fastener is closed and the compression bands are individually tightened so that the entire assembled therapeutic compression device applies the desired compression to the portion of the body or limb.

When it is desired to remove the assembled therapeutic compression device, the compression bands can be loosened without unthreading the ends of the compression bands and the slide fastener can be opened to separate the longitudinal portions 15a as shown in FIG. I. When the assembled therapeutic compression device is to be reapplied, the slide fastener can be quickly closed and the desired compression reapplied by tightening the compression bands one by one.

Figure 1:
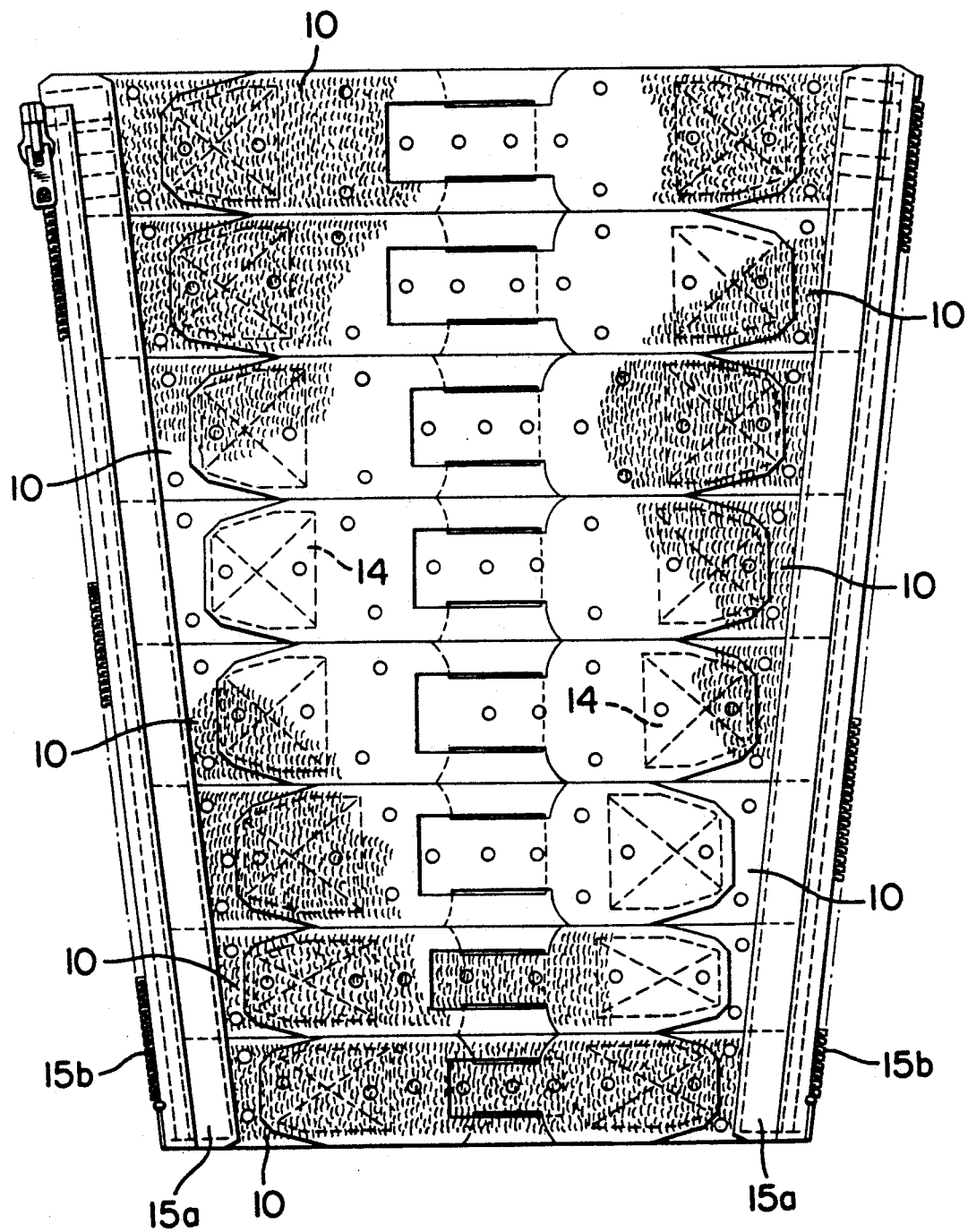
FIG. 1 is a front view of a therapeutic device made up of a plurality of compression bands arranged in parallel, edge-to-edge relationship with the slide fastener splicing band separated.

Although the slide fastener splicing band as shown in FIG. 1 is capable of completely separating the longitudinal portions 15a, in some cases it may be possible to use a slide fastener of the type that separates at one end only of the splicing band. For example, when the therapeutic device is applied to a leg, the separated end of the slide fastener can be at the bottom where the circumference of the leg is much smaller than the circumference encompassed at the upper end of the assembled therapeutic device in which case the device can be removed by sliding it over the foot.

To reapply the assembled legging, the legging is ordinarily rotated to place the slide fastener at the front so that the slide fastener can be easily engaged. The legging is then rotated to position the engaged slide fastener at the rear of the leg, the engaged slide fastener is closed and the compression bands are tightened at the front.

The invention has been described in preferred forms and by way of example only, and many variations and modifications can be made therein within the spirit of the invention. The invention, therefore, is not intended to be limited any specified form or embodiment, except insofar as such limitations are expressly set forth in the claims.

I claim:

1. A body or limb encircling therapeutic device including a plurality of body or limb encircling compression bands, each band having a slot at one end and a narrow portion at the other end, the narrow portion of the band being inserted through the slot to tighten the band on the body or limb, fastening surfaces on the inner surfaces of the both ends of each band and on the outer surface of each band to hold the band in tightened condition, each band further having an intermediate span removed to adjust its length, leaving cut ends to be spliced, and a longitudinally extending splicing band which has a fastening surface on one side to interlock with and splice the cut ends of the compression bands, said splicing band being separable into two longitudinally extending parts, and fastening means carried by the parts to separate and reconnect the longitudinal parts while the longitudinal parts remain fastened to the cut ends of the compression bands to maintain the compression bands in assembled condition when the fastening means has separated the longitudinal parts.

2. A slide fastener band for splicing together cut ends of a plurality of substantially parallel therapeutic compression bands having fastening surfaces, the slide fastener splicing band being arranged in perpendicular relationship to the bands, the width spanning the cut ends of the compression bands and holding them together for application to a body or limb to be encircled by the bands, the slide fastener splicing band comprising a pair of longitudinally extending portions, fastening surfaces on the longitudinally extending portions which interlock with the fastening surfaces of the therapeutic compression bands to be spliced and held together in substantially edge-to-edge relationship and a slide fastener operable to join and separate the longitudinally extending portions for a quick and easy removal of the compression bands from the body or limb which they encircle and for reapplication of the assembled therapeutic compression bands around the body or limb.

3. In a body or limb encircling therapeutic device which includes a plurality of body or limb encircling compression bands for application to a body or a limb in substantially parallel, edge-to-edge relationship, fastening inner surfaces at opposite ends of each band and a fastening outer surface on each band, the fastening inner surfaces interlocking with the fastening outer surface when the compression band is tightened and the fastening surfaces are pressed together, the improvement of a slide fastener splicing band to be applied perpendicularly to the parallel compression bands with the width spanning cut ends of the compression bands to be spliced, the slide fastener splicing band comprising a pair of longitudinally extending portions having fastening surfaces which interlock with the outer fastening surface of the compression bands, thereby holding the compression bands together in an assembly for application to the body or limb to be encircled thereby, and a slide fastener intermediate the longitudinally extending portions for separating and joining the longitudinally extending portions to facilitate removal of the compression bands from the body or limb which they encircle while holding the compression bands assembled together.

4. A body or limb encircling therapeutic device including a plurality of body or limb encircling compression bands, each band having a slot at one end and a narrow portion at the other end, the narrow portion of the band being inserted through the slot to tighten the band on the body or limb, fastening surfaces on the inner surfaces of the both ends of each band and on the outer surface of each band to hold the band in tightened condition, and a slide fastener splicing band which includes a longitudinally extending slide fastener, a pair of longitudinal portions of the slide fastener splicing band and fastening surfaces on the longitudinally extending portions which interlock with and splice cut ends of the compression bands.

5. A body or limb encircling therapeutic device comprising a plurality of body or limb encircling bands, each band having a slot at one end and a narrow portion at the opposite end, the narrow portion of the band being inserted through the slot to tighten the band on the body or limb, fastening surfaces on the inner sides of both ends of each band and on the outer side of each band to interlock and hold the band in tightened condition, a slide fastener splicing band having a longitudinally extending slide fastener which joins and separates longitudinal portions of the slide fastener splicing band and fastening surfaces on the longitudinally extending portions which interlock with the outer fastening surfaces of the compression bands to be spliced so that when intermediate portions of the compression bands have been removed to shorten the bands to accommodate the girth of the body or limb to be encircled, the cut ends are spliced by applying the slide fastener splicing band perpendicularly to the outer surfaces of the parallel compression bands with the width spanning the cut ends.

* * * * *